United States Patent
Evans

(10) Patent No.: US 6,277,329 B1
(45) Date of Patent: Aug. 21, 2001

(54) DISSOLVED HYDROGEN ANALYZER

(75) Inventor: Patrick J. Evans, Seattle, WA (US)

(73) Assignee: Camp Dresser & McKee Inc., Cambridge, MA (US)

( * ) Notice: Subject to any disclaimer, the term of this patent is extended or adjusted under 35 U.S.C. 154(b) by 0 days.

(21) Appl. No.: 09/273,958

(22) Filed: Mar. 22, 1999

(51) Int. Cl.[7] .............................. B32B 27/04; B32B 27/12; B32B 5/02; G01N 33/18; G01N 1/22

(52) U.S. Cl. ............................... 422/80; 422/94; 422/98; 422/88; 73/19.1; 73/19.12

(58) Field of Search .................................. 422/80, 94, 98, 422/88; 73/31.07, 19.1, 19.12

(56) References Cited

U.S. PATENT DOCUMENTS

| | | |
|---|---|---|
| 3,661,010 | 5/1972 | Neuwelt . |
| 3,920,396 | 11/1975 | Schuy . |
| 3,922,904 | * 12/1975 | Williams et al. .......................... 73/19 |
| 4,111,036 | * 9/1978 | Frechette et al. ......................... 73/23 |
| 4,236,404 | 12/1980 | Ketchum et al. . |
| 4,344,918 | * 8/1982 | Takahashi ............................... 422/80 |
| 4,916,079 | 4/1990 | Baillie et al. . |
| 5,152,963 | * 10/1992 | Wreyford ................................ 422/80 |
| 5,279,795 | 1/1994 | Hughes et al. . |
| 5,364,594 | * 11/1994 | Johnson et al. ......................... 422/90 |
| 5,476,637 | * 12/1995 | Fuhrmann ............................ 422/68.1 |
| 5,522,915 | * 6/1996 | Ono et al. ................................ 75/385 |
| 5,798,271 | * 8/1998 | Godec et al. ........................... 436/146 |
| 6,123,904 | * 9/2000 | Wright et al. ........................... 422/80 |
| 6,138,497 | * 10/2000 | Nix et al. ............................... 73/19.06 |

FOREIGN PATENT DOCUMENTS 0 122 511 A2    10/1984  (EP) .

OTHER PUBLICATIONS

Chapelle, F.H. et al., "Geochemistry of dissolved inorganic carbon in a Coastal Plain aquifer. 1. Sulfate from confining beds as an oxidant in microbial $CO_2$ production," *J. Hydrol.*, 127:85–108 (1991).

Lundström, I., "Hydrogen Sensitive MOS–Structures Part 1: Principles and Applications," *Sensors and Actuators*, 1:403–426 (1981).

(List continued on next page.)

*Primary Examiner*—Jill Warden
*Assistant Examiner*—B. R Gordon
(74) *Attorney, Agent, or Firm*—Christensen O'Connor Johnson Kindness PLLC

(57) ABSTRACT

The present invention provides apparatuses and processes for the measurement of hydrogen in aqueous solution at concentrations as low as about 0.1 nM. The present invention is capable of accurately and reproducibly measuring the concentration of dissolved hydrogen in an aqueous solution that also contains other dissolved gases, such as oxygen, carbon monoxide and sulfur compounds, such as hydrogen sulfide. In a presently preferred embodiment of a hydrogen analyzer 38 of the present invention, water containing dissolved hydrogen is equilibrated with a carrier gas by means of gas flow through a mass transfer device 10. Carrier gas is equilibrated with hydrogen from the water within a gas equilibration volume 4 and is then circulated, by means of a pump 1, through a circuit 14 that includes a moisture removal component 16, an oxygen removal component 15 and a heated carbon monoxide and sulfur compound removal component 17, which remove water, oxygen, carbon monoxide and sulfur compounds from the carrier gas without consuming or producing hydrogen. A sensor 7 measures the amount of hydrogen in the carrier gas from which moisture, oxygen, carbon monoxide and sulfur compounds have been removed.

19 Claims, 4 Drawing Sheets

OTHER PUBLICATIONS

Robinson, J.A. et al., "Method for Measuring Dissolved Hydrogen in Anaerobic Ecosystems: Application to the Rumen," *Applied and Environmental Microbiology*, 41(2):545–548 (1981).

Pauss, A. et al., "Continuous Measurement of Dissolved $H_2$ in an Anaerobic Reactor Using a New Hydrogen/Air Fuel Cell Detector," *Biotechnology and Bioengineering*, 35:492–501 (1990).

Lundström, K.I. et al., "A hydrogen–sensitive Pd–gate MOS transistor," *J. Applied Physics*, 46(9):3876–3881 (1975).

Butler, M.A. et al., "Fiber Optic Hydrogen Sensor," *Sandia Report*, pp. 1–56 (1996).

Strong, G.E. et al., "An In Situ Dissolved–Hydrogen Probe for Monitoring Anaerobic Digesters Under Overload Conditions," *Biotechnology and Bioengineering*, 45:63–68 (1995).

Dornseiffer, P. et al., "Modeling of Anaerobic Formate Kinetics in Mixed Biofilm Culture Using Dynamic Membrane Mass Spectrometric Measurement," *Biotechnology and Bioengineering*, 45:219–228 (1995).

Hanus, F.J. et al., "Techniques for Measurement of Hydrogen Evolution by Nodules," *Methods in Enzymology*, 69:731–739 (1980).

Istok, J.D. et al., "Single–Well, "Push–Pull" Test for In Situ Determination of Microbial Activities," *Groundwater*, 25(4):619–631 (1997).

Gibeault, J.–P. et al., "New Instruments to Measure and Monitor Dissolved Hydrogen in Water," *Transactions of the American Nuclear Society*, 46:612–613 (1984).

Liu, C. et al., "An Advanced Pd/Pt Relative Resistamce Sensor for the Continuous Monitoring of Dissolved Hydrogen in Aqueous Systems at High Subcritical and Supercritical Temperatures," *J. Supercritical Fluids*, 8:263–270 (1995).

Westinghouse Electric Corporation, "Hydrogen–Evolution Monitoring as a Measure of Steam–Generator Corrosion," Research Project, Final Report (1992).

Stiblert, L. et al., "Hydrogen leak detector using a Pd–gate MOS transistor," *Rev. Sci. Instrum.*, 46(9):1206–1208 (1975).

* cited by examiner

DISSOLVED HYDROGEN ANALYZER

DISSOLVED HYDROGEN ANALYZER

The U.S. Government may have certain rights in this invention as provided for in SBIR Contract No. F41624-97-C-0005 awarded by the Department of the Air Force.

FIELD OF THE INVENTION

The present invention relates to measurement of dissolved molecular hydrogen. In particular, the present invention relates to an apparatus and process for the measurement of hydrogen in water at concentrations as low as on the order of 0.1 nM.

BACKGROUND OF THE INVENTION

Molecular hydrogen present in water in a dissolved form (dissolved hydrogen) is an important indicator of various biological and chemical processes. These processes include in situ bioremrediation of groundwater by engineered methods or by natural attenuation, anaerobic reactors for waste treatment including anaerobic digesters, anaerobic bioprocesses for the manufacture of biochemicals, including fermentation, operation of subsurface, permeable metal-reactive walls for remediation of chlorinated chemicals in groundwater by reductive dehalogenation and corrosion of metals in process systems including boilers. Dissolved hydrogen can be an indicator of the nature, extent, or stability of these processes.

The concentration of dissolved hydrogen can be extremely low. For example, one class of anaerobic bacteria known as iron-reducing bacteria typically demonstrate dissolved hydrogen concentrations in groundwater in the range of 0.1 to 1.0 nM when at steady state (F. H. Chapelle and P. B. McMahon, J. Hydrology, 127:85–108 (1991)).

Methods available for measurement of dissolved hydrogen involve direct measurement in the liquid of interest or extraction of dissolved hydrogen into a carrier gas which is then analyzed. Only one method exists for measuring dissolved hydrogen concentrations as low as 0.1 nM and is called the "bubble strip" method (F. H. Chapelle and P. B. McMahon, J. Hydrology, 127:85–108 (1991)). This method involves equilibration of a bubble of nitrogen with a flowing stream of groundwater in a gas sampling bulb made from glass. Samples of the gas bubble are injected into a reduction gas analyzer over time until the gas bubble is in equilibrium with the groundwater. The reduction gas analyzer employs chemical reduction of a heated bed of mercuric oxide by hydrogen to form gaseous mercury that is sensed by an ultraviolet detector. Chromatographic separation of hydrogen from other reducing gases is required prior to mercuric oxide reduction. The gaseous hydrogen concentration is then related to the dissolved hydrogen concentration by Henry's law where 0.1 nM dissolved hydrogen approximately correlates to 0.125 ppm of gaseous hydrogen at equilibrium and ambient temperature and pressure. This method is difficult, time-consuming, and expensive to use and has therefore not gained widespread acceptance as an analytical method. Application of the reduction gas analyzer, in combination with hydrogen equilibration over Teflon tubing, to anaerobic digestion in particular is cited as being limited because of its "sophistication, high cost, detection limits, and interference from other solutes" (K. Kuroda, R. G. Silveira, N. Nishio. H. Sunahara, and S. Nagai, J. Ferment. Boeing, 71:418–423 (1991)). The gas bubble equilibration method also is greatly subject to operator error, in part because of mass transfer limitations. A. Pauss, G. Andre, M. Perrier, and S. R. Guiot, Appl. Environ Microbiol, 56:1636–1644 (1990). Other methods that are available for hydrogen measurement are insensitive at these low concentrations and in environments of interest.

A Clark probe with reversed polarity is capable of hydrogen measurement in gases or liquids. The lower detection limit is 500 ppm in gases (F. J. Hanus, K. R. Carter, and H. J. Evans, Methods in Enzymology, 69:731–739 (1980)) and 15 $\mu$g/L (7,500 nM) in water (J. D. Istok, M. D. Humphrey, M. H. Schroth, M. R. Hyman, and K. T. O'Reilly, Ground Water, 35:619–631 (1997)). Another electrochemical probe for dissolved hydrogen described by Strong (G. E. Strong and R. Cord-Ruwisch, BiotechnoL Boeing, 45:63–68 (1995)) has a detection limit of 30 Pa partial pressure which is equivalent to 240 nM. Ozawa et al. in EP 0096417A1 describe an electrochemical hydrogen sensor that has a sensitivity of 500 nM dissolved hydrogen. Kitamura et al. in EP 0122511 A2 describe a similar electrochemical hydrogen sensor that compensates for oxygen but does not remove its influence and has an insufficient sensitivity in the nM range. Other electrochemical methods employing fuel cells have been described with detection limits of 1 $\mu$M (1,000 nM) (J.-P. Gebeault, J. Van Berlo, and M. Dymarski, Trans. Amer. Nucl Soc., 46:612–613 (1984)) and 80 nM. A. Pauss, R. Samson, S. Guiot and C. Beauchemin, Biotechnol. Bioeng., 35:492–501 (1990). Hydrogen sulfide and oxygen interfere with the performance of these probes. A. Pauss, R. Samson, S. Guiot and C. Beaucherun, Biotechnol. Bioeng., 35:492–501 (1990). In one case, oxygen did not interfere as long as it was present in lower concentrations than hydrogen (N. Hara and D. D. Macdonald, J. Electrochem. Soc., 144:4152–4157 (1997)). In the practice of the present invention, very low hydrogen concentrations render this requirement impractical.

Gas chromatography with thermal conductivity detection can be used to detect hydrogen in gases. This method can be used to detect 0.5 nmoles of injected hydrogen (F. J. Hanus, K. R. Carter, and H. J. Evans, Methods in Enzymology, 69:731–739 (1980)) which, based on a 1-ml injection, translates to a concentration of 12 ppm in gas or an equilibrium dissolved concentration of 9.6 nM.

An instrument based on thermal conductivity has been developed to measure hydrogen in steam or hydrogen dissolved in water and has an inadequate detection limit of 100 nM (C. R. Wilson, Electric Power Research Institute Report NP-2650 (1982)).

Equilibration of dissolved hydrogen in water with a carrier gas followed by removal of coexisting gases (e.g., oxygen, hydrogen sulfide, carbon dioxide) that can interfere with or dilute hydrogen during analysis has been attempted but not at sufficiently low detection limits. Removal of carbon dioxide from carrier gas equilibrated with rumen fluid followed by gas chromatography resulted in a detection limit of 10 nM (J. A. Robinson, R. F. Strayer, and J. M. Tiedje, Appl. Environ. Microbiol, 41:545–548 (1981)). This method is not applicable where carbon dioxide is present in low concentrations.

Mass spectrometry can be used to detect hydrogen in gases or, via use of a membrane system, in liquids (P. Dornseiffer, B. Meyer, and E. Heinzle, Biotechnol. Bioeng., 45:219–228 (1995)). Hydrogen concentrations detected in liquids are in the low $\mu$M (1,000 nM) range and accurate measurement can be compromised by biofilm growth on the membrane surface which requires periodic maintenance and cleaning.

A palladium-coated micromirror fiber optic sensor developed by Sandia National Laboratories was shown to be capable of sensing 50 ppm of hydrogen in transformer oil (M. A. Butler, R. Sanchez, and G. R. Dulleck, Sandia Report SAND96-1133. UC-706 (1996)).

Various types of solid state sensors are capable of hydrogen detection. eithley (Cleveland, Ohio) sells a hot wire semiconductor type sensor named CH-H. This sensor contains a platinum wire in a sintered tin oxide semiconductor bead. Hydrogen reacts with oxygen on the platinum wire thereby generating heat. The altered resistance of the platinum wire is sensed in a bridge circuit. This sensor requires the presence of oxygen and is sensitive to approximately 10 ppm hydrogen in gas or an equilibrium dissolved concentration of 8 nM.

Sensors based on the observed change in the electrical resistance of platinum and palladium upon adsorption of hydrogen have been described. These sensors can be immersed in water but have a detection limit of 5,000 nM dissolved hydrogen (C. Liu and D. D. Macdonald, *J. Supercritical Fluids.*, 8:263–270 (1995)).

Lundstrom described metal oxide semiconductor (MOS) transistors containing a palladium gate (K. I. Lundstrom, M. S. Shivaraman, and C. M. Svensson, *J. Appl. Physics.*, 46:3876–3880 (1975); I. Lundstrom, *Sensors and Actuators.*, 1:403–426 (1981)). The sensitivity of these structures to hydrogen in gas is highly dependent on oxygen concentration. A 10 mV response was observed with 0.5 ppm hydrogen in air and with 0.03 ppb hydrogen in an inert gas such as argon or nitrogen. The difference in response is due to the oxygen content of air. These sensors are also sensitive to hydrogen sulfide albeit at ten-fold greater concentrations than hydrogen (I. Lundstrom, *Sensors and Actuators.*, 1:403–426 (1981)) and sulfur compounds are well known for their poisoning of metallic surfaces. A hydrogen leak detector based on such MOS sensors demonstrated a practical sensitivity of 1 ppm (L. Stiblert and C. Svensson, *Rev. Sci. Instrum.*, 46:1206–1208 (1975)).

A hydrogen sensor with a practical sensitivity of 1 ppm in gas is described by Hughes et al. in U.S. Pat. No. 5,279,795. This type of sensor is disadvantageous in part because of the slow response at low hydrogen concentrations. The sensitivity of this sensor is negatively affected by the presence of oxygen. It was reported that hydrogen sulfide does not poison the sensor; however, the tests were conducted in air where hydrogen sulfide poisoning is known to be mitigated by oxidation. This sensor has been incorporated into a hand held detector by DCH Technology which has a detection limit of 10 ppm in gas or an equilibrium dissolved concentration of 8nM.

Immersion of MOS devices in anaerobic water is not practical because of incompatibility. Protection of a MOS device with a gas-permeable membrane such as Goretex™ would be expected to work for detection of dissolved hydrogen in anaerobic water but does not. While anaerobic conditions in groundwater would seem to imply the absence of oxygen; in fact, oxygen is often observed in "anaerobic" groundwater, presumably due to the heterogeneous nature of many aquifers. Additionally, MOS devices are poisoned by hydrogen sulfide. Hydrogen sulfide is a common contaminant present in anaerobic groundwater and in anaerobic digesters. These sensors are also inhibited by carbon monoxide which is found in anaerobic environments.

Neuwelt in U.S. Pat. No. 3,661,010 describes a method employing an electrochemical sensor covered by a membrane over which flows the liquid. This method is disadvantageous because no method for removal of interferences is provided and insufficient sensitivity exists. A dissolved hydrogen analyzer manufactured by Orbisphere Laboratories (Inverness, Calif.) also uses an electrochemical sensor covered by a membrane but is sensitive only to 15 nM dissolved hydrogen and this sensitivity is adversely affected by oxygen.

Immersion of any type of hydrogen probe in a biological medium can also result in growth of biofihm on the probe. Such biofilm growth can subsequently result in dissolved hydrogen consumption or production which can affect the measurement accuracy. Such effects were observed with a gas diffusion probe used in conjunction with a reduction gas analyzer (H. Kramer and R. Conrad, *FEMS Microbiol. Ecol.*, 12:149–158 (1993)).

Schuy in U.S. Pat. No. 3,920,396 describes a membrane equilibration device that uses an extraction gas circulating in a closed loop to attain equilibrium between the gas and liquid sample of fixed volume. This method is disadvantageous because dissolved gases with high Henry constants will be predominately stripped into the gas phase, and the attained equilibrium will occur at a dissolved gas concentration that is significantly less than the original dissolved gas concentration. Furthermore, this method provides no means for removal of interfering gases that also equilibrate across the membrane.

Baillie et al. in U.S. Pat. No. 4,916,079 describe a gas-liquid equilibration device that uses a constant flow of liquid which overcomes the disadvantages of U.S. Pat. No. 3,920,396 by using a continuous flow of liquid and spiking the equilibration gas with a known quantity of the analyte to overcome interferences. This method is not applicable to the analysis of low levels of hydrogen in the practice of the present invention because the concentrations of hydrogen are too low relative to the concentrations of interfering gases.

Ketchum et al. in U.S. Pat. No. 4,236,404 describe a device to monitor hydrogen and other gases in electrical insulating liquids such as transformer oils that employs equilibration between gas and liquid and a thermal conductivity detection gas chromatography for analysis. This device overcomes interferences by chromatographic separation but does not have sufficient sensitivity for the low-concentration applications contemplated by this invention.

Thus, to the best of applicant's knowledge no practical device capable of detecting concentrations on the order of 0.1 nM dissolved hydrogen exists with the sole exception of the reduction gas analyzer which is expensive and must be used in combination with the bubble strip method which is difficult to use.

SUMMARY OF THE INVENTION

The present invention provides apparatuses and processes for the measurement of hydrogen in aqueous solution at concentrations of less than 1.0 nM, and preferably as low as about 0.1 nM. The present invention is capable of accurately and reproducibly measuring the concentration of dissolved hydrogen in an aqueous solution that may also contain other dissolved gases, such as oxygen, carbon monoxide and sulfur compounds, such as hydrogen sulfide.

In one aspect, the present invention provides a hydrogen analyzer that is capable of accurately measuring the amount of hydrogen in aqueous solution at concentrations of less than 1.0 nM, and preferably as low as about 0.1 nM. The hydrogen analyzer includes a mass transfer device, having an aqueous portion through which passes an aqueous analyte, such as contaniated ground water, and a gaseous portion, through which passes a carrier gas, such as nitrogen gas. Within the mass transfer device, hydrogen gas is transferred from the aqueous analyte to the carrier gas. The hydrogen analyzer also preferably includes a gas equilibrium volume within which hydrogen gas transferred from the aqueous analyte is equilibrated with the carrier gas. The hydrogen analyzer also preferably includes a component for removal of carbon monoxide from the carrier gas containing hydrogen; a component for removal of sulfur compounds from the carrier gas containing hydrogen; a component for removal of oxygen from the carrier gas containing hydrogen; and a hydrogen sensor for measuring the amount of hydrogen in the carrier gas. Preferably the carbon monoxide removal component and the sulfur compound removal component are unitary, i.e., are not physically separate components. Preferably the hydrogen analyzer also includes a water removal component The foregoing components of the hydrogen analyzer of the present invention are in gaseous communication, for example by means of tubes or pipes, and a pump moves the carrier gas through the components of the hydrogen analyzer.

Carbon monoxide removal is necessitated because of the generation of carbon monoxide during the removal of oxygen in accordance with the preferred method of the present invention. Alternative methods of oxygen scavenging may be adapted for use in the present invention, however, which do not generate carbon monoxide, in which case a carbon monoxide removal component is not required. Likewise sulfur and water removal are only necessitated when present in the carrier gas.

In a presently preferred embodiment of the hydrogen analyzer of the present invention, water containing dissolved hydrogen is equilibrated with a carrier gas by means of gas flow through the mass transfer device. Equilibrated carrier gas within the gas equilibration volume is then circulated, by means of the pump, through a circuit that includes the moisture removal component, the oxygen removal component and a heated carbon monoxide and sulfur compound removal component, which remove water, oxygen, carbon monoxide and sulfur compounds from the carrier gas without consuming or producing hydrogen. Preferably the moisture removal cartridge is located before the carbon monoxide and sulfur compound removal cartridge in the gas flow path. A sensor measures the amount of hydrogen in the carrier gas from which moisture, oxygen, carbon monoxide and sulfur compounds have been removed.

The mass transfer device can be any device that allows equilibration of dissolved hydrogen with the carrier gas phase. Examples of acceptable mass transfer devices include hollow fiber gas transfer modules and sparging devices. Presently preferred moisture-removal compositions, for inclusion in the moisture removal component, are molecular sieves and calcium sulfate compositions.

Presently preferred carbon monoxide removal compositions, for inclusion in the carbon monoxide removal component, are metal oxide catalysts including those based on copper and zinc, such as the finely dispersed cupric oxide catalyst named R3–11, manufactured by BASF (Parsipany, N.J.). Preferably the carbon monoxide removal composition includes a colorimetric carbon monoxide indicator. The carbon monoxide removal component also preferably includes a heater for heating the carbon monoxide removal composition within. Preferably the carbon monoxide composition is also capable of adsorbing sulfur compounds. A presently preferred carbon monoxide removal composition that is also capable of adsorbing sulfur compounds is catalyst R3–11.

The oxygen removal component can contain any composition that is capable of efficiently and rapidly removing oxygen from the carrier gas without producing or consuming hydrogen. Presently preferred oxygen removal compositions are based on ascorbic acid.

Presently preferred hydrogen-sensing components include metal oxide semiconductors, such as Shottky diodes and field effect transistors (FET) having a palladium gate. The Shottky diode in the presently preferred embodiment of the hydrogen analyzer of the invention is capable of detecting hydrogen dissolved in water at concentrations from about 0.1 nM to about 100 nM. It is theorized that greater concentrations of up to 1,000,000 nM are easily detectable using different hydrogen-sensing components.

In another aspect, the present invention provides processes for measuring the amount of hydrogen in an aqueous solution including the steps of: (1) equilibration of water containing dissolved hydrogen with a carrier gas; (2) removal of oxygen and, where present, carbon monoxide, moisture and sulfur compounds from the carrier gas containing hydrogen; and (3) measuring the amount of hydrogen in the carrier gas that has been treated to remove oxygen, carbon monoxide, moisture and sulfur compounds. Step 2 of the processes of the present invention preferably further includes removal of moisture from the carrier gas containing hydrogen. The processes of the present invention neither consume nor produce hydrogen. Preferably a solid state sensor is used to measure the concentration of hydrogen. A presently preferred method of measuring hydrogen concentration is by monitoring an output voltage from the solid state sensor and calculating the rate of voltage increase.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

The present invention provides apparatuses and processes for the measurement of hydrogen in aqueous solution at concentrations as low as about 0.1 nM. The apparatuses and processes of the present invention are capable of accurately and reproducibly measuring the concentration of dissolved hydrogen in an aqueous solution that may also contain other dissolved gases, such as oxygen, carbon monoxide and sulfur compounds.

Figure 1:
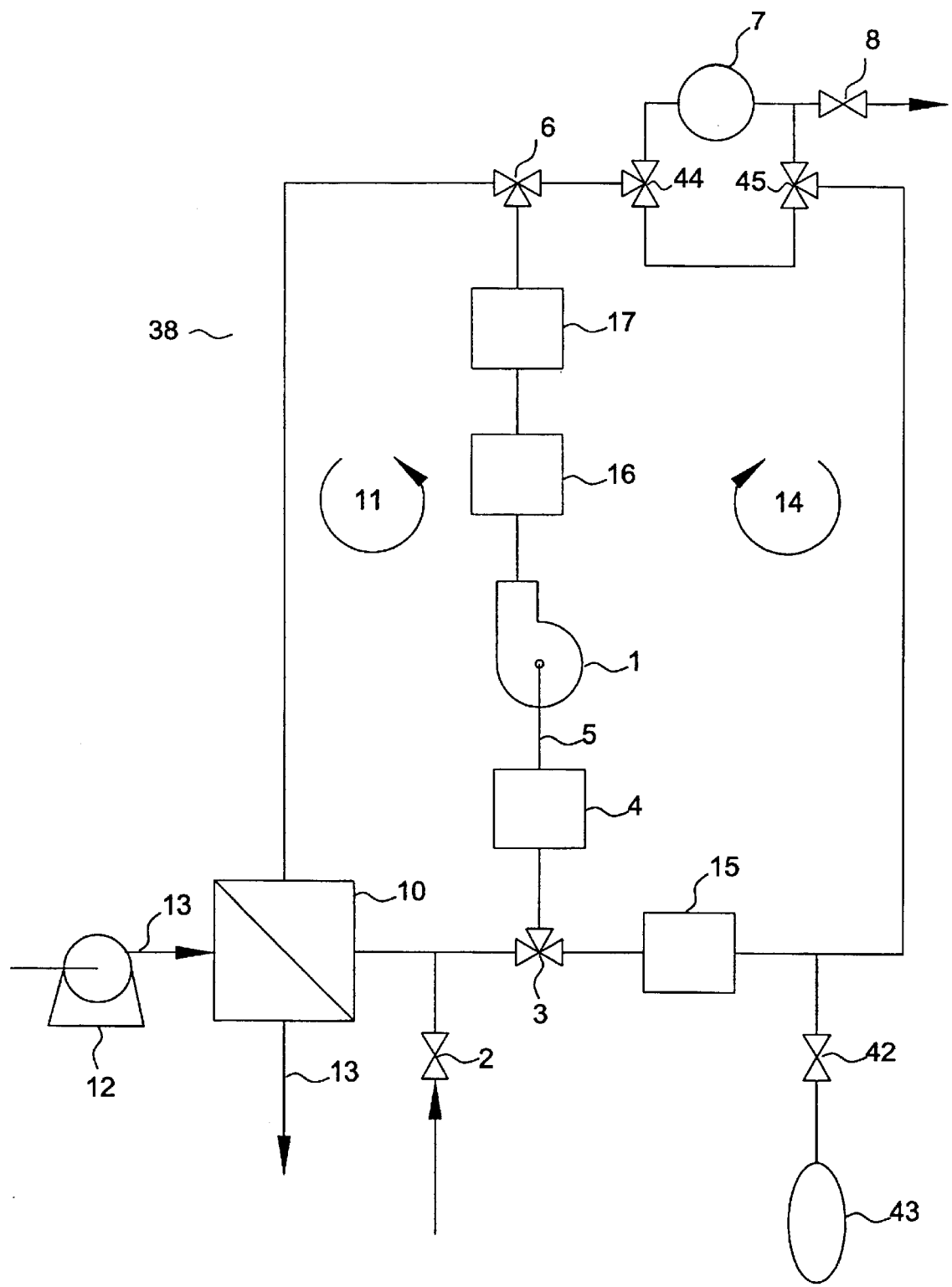
FIG. 1 shows a circuit diagram representing a presently preferred configuration of the hydrogen analyzer of the present invention.

FIG. 1 shows a presently preferred configuration of a hydrogen analyzer 38 of the present invention. Hydrogen analyzer 38 includes a hydrogen sensor 7, a mass transfer device 10, a gas reservoir 4, an oxygen removal cartridge 15, a moisture removal cartridge 16, and a carbon monoxide and sulfur compound removal cartridge 17. In a preferred embodiment of the present invention, the carbon monoxide and sulfur compound removal cartridge 17 serves as the gas reservoir 4, in which case a separate reservoir is not required. In operation, water containing dissolved hydrogen, is equilibrated with a carrier gas by means of gas flow in a first flow circuit 11. Equilibrated carrier gas within gas equilibration volume 4 is then circulated through a second flow circuit 14 during which oxygen, water, carbon monoxide, and sulfur compounds are removed from the carrier gas without consuming or producing hydrogen. Sensor 7 then measures the amount of hydrogen in the carrier gas.

With reference again to FIG. 1, during the sensor preparation stage, called Stage A, air pump 1 pulls air in through first solenoid valve 2 and second solenoid valve 3 and gas reservoir 4 via tubing 5. The air is then discharged from pump 1 through moisture removal cartridge 16, heated carbon monoxide and sulfur compound removal cartridge 17, third solenoid valve 6 and fourth solenoid valve 44, and hydrogen sensor 7 prior to being discharged to the atmosphere through fifth solenoid valve 8. The purpose of Stage A is to allow residual hydrogen present on sensor 7 to be oxidized by oxygen present in air. Presence of residual hydrogen on sensor 7 is typically indicated by a sensor output voltage that does not return to its baseline voltage following exposure to hydrogen. Residual hydrogen on the sensor is especially problematic in oxygen-free gas, such as is generated within hydrogen analyzer 38 of the present invention.

The length of Stage A is dependent on the characteristics of sensor 7. In the case of a metal-oxide semiconductor Shottky diode with a palladium/silver gate and an alumina insulator, a one-minute Stage A is usually sufficient but may need to be longer. Preconditioning may be required regularly or intermittently with specific sensors 7. These preconditioning steps may include exposure to nitrogen or hydrogen at various temperatures for various times and will be dependent on the specific nature of sensor 7.

With reference again to FIG. 1, during Stage B, which is referred to as the nitrogen purge stage and which follows Stage A, nitrogen gas is used to purge air and traces of hydrogen from oxygen removal cartridge 15, tubing 5, gas reservoir 4, moisture removal cartridge 16, and heated carbon monoxide and sulfur compound removal cartridge 17. Alternately, other methods of hydrogen removal can be utilized within the scope of the present invention, such as a thermal oxidizer. The purpose of Stage B is to remove traces of hydrogen that can interfere with quantification of low concentrations of dissolved hydrogen in an aqueous sample that is being analyzed. Nitrogen enters through sixth solenoid valve 42 from cylinder 43 and passes through oxygen removal cartridge 15, second solenoid valve 3, gas reservoir 4, tubing 5, pump 1, moisture removal cartridge 16, heated carbon monoxide and sulfur compound removal cartridge 17, third solenoid valve 6 and fourth solenoid valve 44, and sensor 7, and exits through fifth solenoid valve 8.

Stage C follows Stage B and is referred to as the hydrogen equilibration stage during which hydrogen gas in the aqueous sample being analyzed is equilibrated with the carrier gas in gas reservoir 4 and first flow circuit 11. With reference again to FIG. 1, in Stage C sixth solenoid valve 42 and fifth solenoid valve 8 close and third solenoid valve 6 changes direction to promote flow in first flow circuit 11 through air pump 1, cartridges 16 and 17, third solenoid valve 6, the gas side of mass transfer module 10, second solenoid valve 3, and gas reservoir 4. The aqueous sample being analyzed is pumped through the liquid side of gas transfer module 10 by pump 12 via tubing 13. The duration of time allowed for Stage C is determined by the time required for hydrogen in the aqueous sample being analyzed to equilibrate with the carrier gas in gas reservoir 4 and first flow circuit 11. Stage C time is typically in the range of 1–10 minutes. The void volumes of moisture removal cartridge 16 and sulfur compound removal cartridge 17 can serve as an equivalent gas reservoir 4, if desired.

Mass transfer module 10 can be any device that allows equilibration of dissolved hydrogen with the carrier gas phase. Mass transfer module 10 is preferably constructed from hollow fiber gas transfer modules or sparging devices. These hollow fiber modules are composed of a plurality of hollow fiber membranes encased in a shell with integral manifold. The manifold mechanically supports the ends of the hollow fiber membranes and directs carrier gas in and out of the lumens of the hollow fiber membranes. The shell surrounds the hollow fiber membranes and directs liquid water past the outer surface of the hollow fiber membranes. Well-designed modules will optimize liquid flow patterns to minimize liquid phase mass transfer resistance. Additionally, well-designed modules will contain hollow fiber membranes that have a high permeability for hydrogen. The sparging devices are designed similarly to a continuous flow gravity settler in which carrier gas is introduced into a flowing liquid via a porous sparging element.

By way of non-limiting example, module GT-0204005 manufactured by NeoMecs (Eden Prairie, Minn.) contains 0.5 square feet of a coated microporous hollow fiber. The gas permeability (P/1) of this membrane is approximately $1 \times 10^4 cm^3/cm^2$-sec-cmHg which is sufficient for the present invention. However, design of the liquid flow pattern is more critical than membrane permeability. Evaluation of the NeoMecs model GT-02010013 module which has 0.13 square feet of the identical membrane was substantially inferior to the model GT-0204005 mainly because of the liquid flow design and not because of the difference in membrane surface area according NeoMecs. A mass transfer time of 1–10 minutes and preferably 2–5 minutes is usually sufficient for equilibration of dissolved hydrogen concentrations up to 10 nM where a NeoMecs GT-0204005 module is used which has 0.5 square feet of membrane surface area and a water flow of 100–1000 milliliters per minute. Water flow is preferably 300–1,000 milliliters per minute. Other mass transfer configurations are suitable and could be readily evaluated by one of ordinary skill in the art without undue experimentation, such as the spargers noted above.

Stage D follows Stage C and is referred to as the carrier gas preparation stage.

During Stage D, oxygen, carbon monoxide, water, and sulfur compounds are removed from the carrier gas, With reference again to FIG. 1, in Stage D, second solenoid valve 3 and third solenoid valve 6 reverse direction and fourth solenoid valve 44 and seventh solenoid valve 45 adjust to promote carrier gas flow through second circuit 14 while bypassing sensor 7. Gas flow through second circuit 14 entails discharge from pump 1 to moisture removal cartridge 16, heated carbon monoxide and sulfur compound removal cartridge 17, third solenoid valve 6, fourth solenoid valve 44 and seventh solenoid valve 45, oxygen removal cartridge 15, second solenoid valve 3, gas reservoir 4, and back to air pump 2. During gas flow through second circuit 14, oxygen, carbon monoxide, water, and sulfur compounds are removed from the carrier gas to levels such that detection of low levels of hydrogen in the carrier gas is possible by hydrogen sensor 7.

Oxygen can be present in the carrier gas due to transfer of oxygen, that is present in the aqueous solution being analyzed, across mass transfer module 10. For example, groundwater that is referred to as "anaerobic", ie., lacking oxygen, may not always be devoid of dissolved oxygen. The presence of dissolved oxygen in "anaerobic" water is an unexpected observation. Traces of dissolved oxygen (ie., less than 1 milligram per liter) can be present in an aqueous solution, especially in groundwater, that is supporting an iron-reducing terminal electron accepting process. This process employs iron-reducing bacteria that can be facultative aerobes and thus can live in the presence of dissolved oxygen. These traces of oxygen prevent sensor 7 from having the required sensitivity to low concentrations of hydrogen. This problem is most notable for iron-reducing terminal electron accepting processes where the typical dissolved hydrogen concentrations are very low, namely 0.1 to 1.0 nM.

Oxygen is removed from the carrier gas by oxygen removal cartridge 15 during Stage D. Oxygen removal cartridge 15 removes oxygen from carrier gas that flows through an oxygen removal composition contained within the module. The oxygen removal composition within oxygen removal cartridge 15 is preferably capable of efficiently and rapidly removing oxygen from the carrier gas without producing or consuming hydrogen. The oxygen removal composition may be composed of any material as long as it possesses the foregoing characteristics. Ascorbic acid-based preparations such as Anaeropack and Anaeropouch manufactured by Mitsubishi Gas Chemical America, Inc. (New York, N.Y.) are the presently preferred oxygen removal compositions. Other oxygen removal compositions useful in the practice of the present invention include, but are not limited to: catalyzed ascorbic acid, alkaline hydroquinone or catechol, catalyzed hydroquinone or catechol, catalyzed sulfite, chelated salicylic acid, and catalyzed dicarboxylic acids. Preferably oxygen removal cartridge 15 will include a colorimetric oxygen indicator.

Oxygen absorbing compositions that are not useful as oxygen removal compositions in the practice of the present invention include: sodium borohydride (produces hydrogen), lithium aluminum hydride (produces hydrogen), carbon monoxide-reduced, finely-dispersed cupric oxide catalyst (adsorbs hydrogen), hydrogen-reduced, finely-dispersed copper catalyst (releases adsorbed hydrogen), iron powder-based preparations (not preferred because is slow and can produce hydrogen via corrosion), heated copper (can produce hydrogen from water via corrosion), lithium-based oxygen scavengers, such as Nanosorb resin (produces hydrogen from water), and zirconium sponge-based oxygen scavengers such as the High Capacity Gas Purifier by Supelco (produces hydrogen from water).

While catalyzed ascorbic acid or alkaline hydroquinone preparations are useful as oxygen removal preparations for use in cartridge 15, their reaction with oxygen results in an unexpected side reaction that forms carbon monoxide. Removal of produced carbon monoxide is required and is accomplished by sulfur compound and carbon monoxide removal cartridge 17. Carbon monoxide is removed so as to prevent interference with measurement of hydrogen by sensor 7. Carbon monoxide removal is required only if generated during the process, such as when using the oxygen removal method of the preferred embodiment of the invention, but may not be required for alternate embodiments of the invention. Carbon monoxide can be present in anaerobic water that contains sulfidogenic or methanogenic bacteria and can be transferred to the carrier gas across gas transfer module 10. For example, carbon monoxide is generated by *Methanosarcina barkeri* during formation of methane and carbon dioxide from acetate where carbon monoxide is an intermediate (G. Gottschalk, *Bacterial Metabolism*, Springer-Verlag, New York. pp. 257–259 (1996)).

Figure 2:
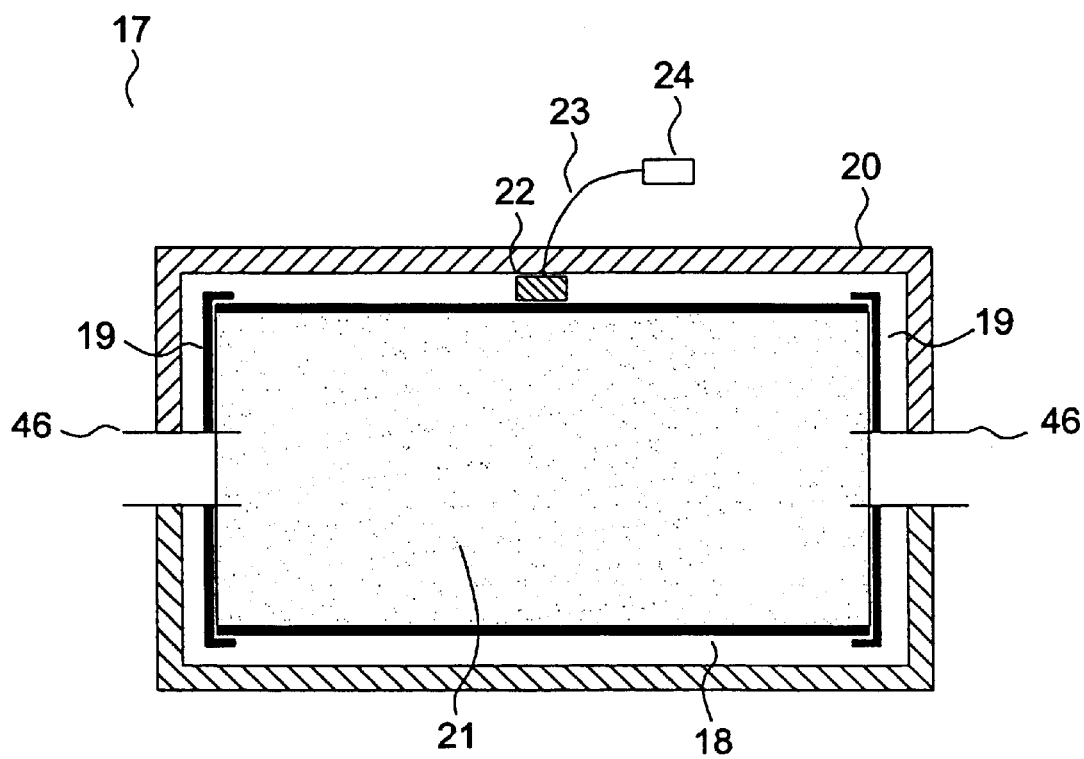
FIG. 2 shows a cross-sectional view of a presently preferred embodiment of carbon monoxide and sulfur compound removal component 17.

FIG. 2 shows a cross-sectional view of a presently preferred design of carbon monoxide removal cartridge 17. Carrier gas flows into and out of carbon monoxide removal cartridge 17 via ports 46. Heat conducting tube 18 and end caps 19 are encased with insulation 20. Carbon monoxide removal composition 21 is contained within tube 18. A preferred carbon monoxide removal composition is a finely dispersed cupric oxide catalyst named R3–11 and manufactured by BASF (Parsippany, N.J.). Metal oxide catalysts including those based on copper and zinc, are suitable for use as a carbon monoxide removal composition in the practice of the present invention. Catalyst R3–11, in its oxidized form, is capable of removing carbon monoxide from carrier gas when heated.

Self-regulating heater 22 heats preparation 21 to the desired temperature when powered by power source 24 that is connected to heater 22 by wires 23. The temperature control is significant because sufficient carbon monoxide removal does not occur at temperatures that are too low and hydrogen generation occurs due to corrosion processes at temperatures that are too high. Preferably the temperature should be between about 45° C. to 90° C., and preferably between about 55° C. and about 80° C. for Catalyst R3–11. The ability of oxidized R3–11 to remove carbon monoxide at these temperatures was not expected based on vendor literature that indicates a minimum temperature requirement of 100° C. Additionally, the vendor literature indicates that hydrogen will also be removed at temperatures greater than 100° C. However, at temperatures between 55° C. and 80° C. carbon monoxide is removed and hydrogen is not removed.

The present inventor discovered that carbon monoxide is adsorbed to R3–11 but is not oxidized to carbon dioxide at temperatures less than 100° C. Hydrogen is not adsorbed on oxidized R3–11 at these temperatures and at room temperature. Interestingly, hydrogen is adsorbed by carbon monoxide-reduced R3–11 at room temperature. These observations were unexpected and resulted in oxidized R3–11 (as opposed to reduced R3–11) having great utility for removal of carbon monoxide in the present invention. Other catalysts useful as carbon monoxide removal compositions in the practice of the present invention include, but are not limited to, Carulite, formerly known as Hopcalite. Carulite is a low-temperature oxidation catalyst composed of manganese dioxide, copper oxide, and aluminum oxide and is manufactured by Carus Chemical Co. (LaSalle, Ill.). Preferably the carbon monoxide removal composition will include a colorimetric carbon monoxide indicator.

Metal oxide, carbon monoxide removal compositions, such as R3–11, when used for carbon monoxide removal in the manner described above, will have a finite lifetime because carbon monoxide is being adsorbed rather than oxidized to carbon dioxide. Eventually the binding sites for carbon monoxide will become saturated and the preparation will have no further capacity for carbon monoxide removal. When saturation of the available binding sites occurs, the carbon monoxide removal composition will require replacement or regeneration. The presence of water vapor also limits the lifetime of metal oxides that are used to remove carbon monoxide. The likely reason is that the metal oxide composition is being used at temperatures below the boiling point of water and thus water vapor condenses on the metal oxide surface and decreases the capacity for carbon monoxide adsorption.

In the practice of the present invention, moisture removal cartridge 16 is preferably included in hydrogen analyzer 38, at a point in first flow circuit 11 and second flow circuit 14 prior to carbon monoxide removal cartridge 17, in order to absorb water from the gas entering cartridge 17, thereby minimizing the replacement frequency of carbon monoxide removal cartridge 17. Moisture removal cartridge 16 can contain any moisture removal preparation as long as it does not consume or generate hydrogen and removes sufficient moisture to prevent premature limitation of the lifetime of carbon monoxide removal cartridge 17. A presently preferred moisture-removal composition for inclusion in moisture removal cartridge 16 is 13× molecular sieves. Calcium sulfate preparations, such as Drierite (W A Hammond Drierite Company, Ltd., Xenia, Ohio), are also useful. Preferably, a colorimetric moisture indicator, such as $CoCl_2$, is included in moisture removal cartridge 16. Placement of moisture removal cartridge 16 in the line of gas flow following oxygen removal cartridge 15 and preceding carbon monoxide removal cartridge 17 is required because certain compositions included in oxygen removal cartridge 15 may release moisture that must be removed from the carrier gas by moisture removal cartridge 16 prior to entering carbon monoxide removal cartridge 17.

Sulfur compounds such as hydrogen sulfide can also interfere with measurement of hydrogen by sensor 7. Sulfur compounds, when present, are more problematic than oxygen and carbon monoxide because they can poison sensor 7 and disable it from further use. One sulfur compound, hydrogen sulfide, is common in anaerobic water because sulfidogenic bacteria can produce it from sulfate. Because hydrogen sulfide is volatile, it is transferred across gas transfer module 10 into the carrier gas.

Sulfur compounds are preferably removed from the carrier gas by carbon monoxide removal cartridge 17 during Stage D. Any composition that is capable of adsorbing sulfur compounds can be included in carbon monoxide removal cartridge 17 so long as it does not consume or produce hydrogen and removes sulfur compounds sufficiently so as to prevent poisoning of sensor 7. Copper oxide catalysts, such as R3–11, are presently preferred for sulfur compound removal and thus serve a dual purpose in the present invention: they can remove carbon monoxide and sulfur compounds simultaneously. Other preferred sulfur adsorbing compounds include, but are not limited to: BASF catalyst R3–12 (Parsippany, N.J.) which includes zinc oxide as well as copper oxide, and hydrated iron oxide. Preferably, a colorimetric sulfur compound indicator is included in carbon monoxide removal cartridge 17.

The duration of Stage D depends, in part, on the identity of the specific compositions used in oxygen removal cartridge 15, moisture removal cartridge 16, and carbon monoxide removal cartridge 17. Based on the presently preferred configuration of hydrogen analyzer 38 of the present invention, the time period for removal of oxygen, sulfur compounds, water, and carbon monoxide from the carrier gas is preferably from about 0.5 minutes to about 10 minutes, more preferably from about 2 minutes to about 4 minutes. Oxygen concentrations should be reduced to less than 0.1% v/v prior to proceeding to the next stage. Carbon monoxide concentrations should be reduced to less than 10 ppm in the carrier gas prior to proceeding to the next stage.

Figure 3:
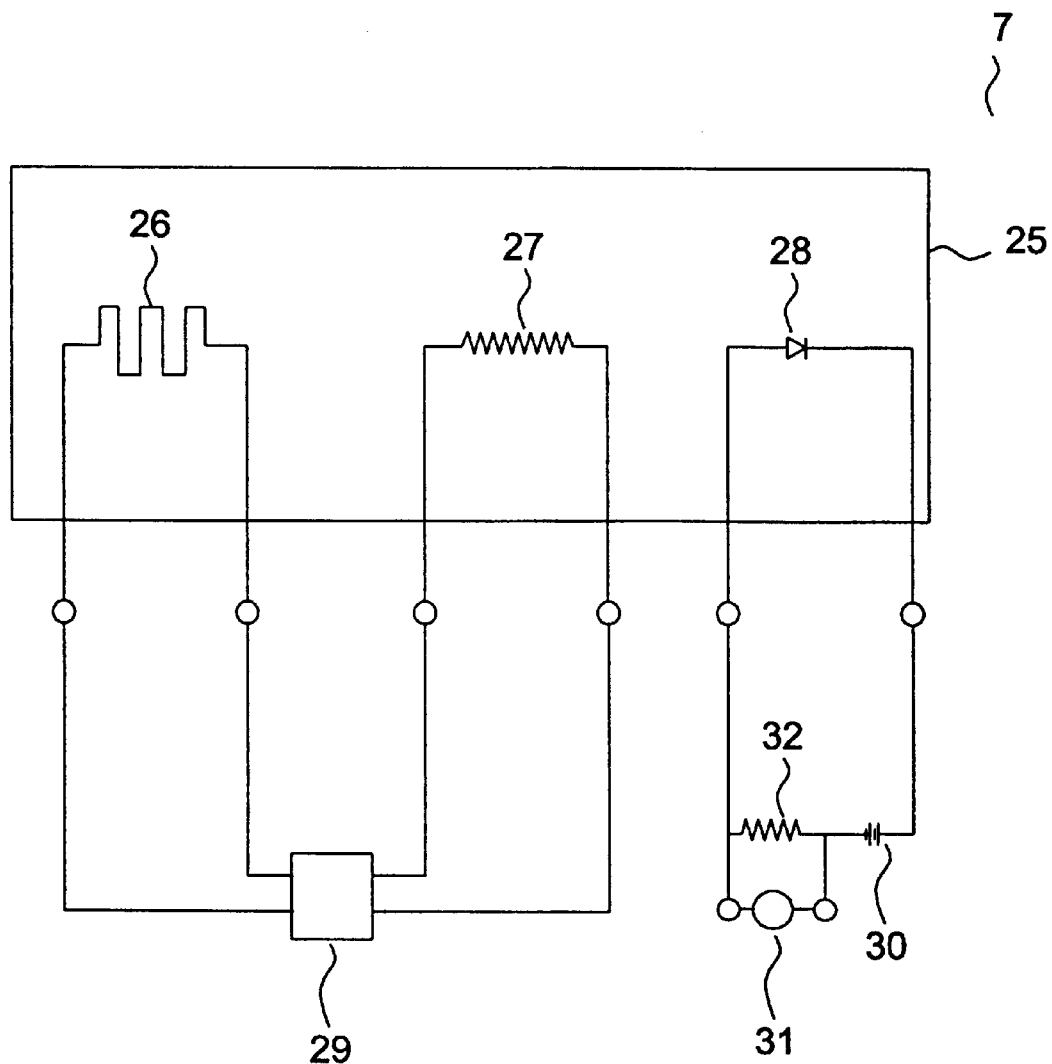
FIG. 3 shows a circuit diagram representing a presently preferred embodiment of hydrogen sensor 7.

Stage E, referred to as the measurement stage, is the final stage during which hydrogen is measured by hydrogen sensor 7. With reference again to FIG. 1, fourth solenoid valve 44 and seventh solenoid valve 45 reverse direction to promote flow past sensor 7 in second flow circuit 14. Sensor 7 is operated by an electrical circuit shown in FIG. 3 during Stages A, B, C, D, and E and data are recorded from sensor 7 during Stage E. FIG. 3 is a schematic representation of sensor 7 and associated electronics that are required for operation of sensor 7 in the presently preferred embodiment of hydrogen analyzer 38 of the present invention. As shown in FIG. 3, a Shottky diode 28 operates as the hydrogen-sensing component of hydrogen sensor 7 in the presently preferred embodiment of hydrogen analyzer 38 of the present invention. Any device that is sensitive to hydrogen at the desired concentrations can be used as the hydrogen-sensing component of hydrogen sensor 7. Another example of a useful hydrogen-sensing device is a field effect transistor (FET) with a palladium gate.

In the presently preferred embodiment, sensor 7 is manufactured using silicon-based microfabrication technology on silicon semiconductor substrate 25 and includes platinum resistance heater 26, platinum resistance temperature detector (RTD) 27, and Shottky diode 28, with a hydrogen-sensitive gate. The Shottky diode is a metal-insulator-semiconductor (MIS) diode with p-type silicon semiconductor, a two-part insulator composed of silica adjacent to the semiconductor and alumina adjacent to the gate, and a metal palladium/silver gate. Substrate 25, including platinum resistance heater 26, platinum resistance temperature detector (RTD) 27, and Shottky diode 28, is manufactured by Case Western Reserve University. Substrate 25, including platinum resistance heater 26, platinum resistance temperature detector (RTD) 27, and Shottky diode 28 are all enclosed in a TO-5 housing. The temperature of sensor 7 is controlled by controller 29 that takes a temperature input from RTD 27 as its process variable and produces an output directed to heater 26 as its control variable. The temperature of sensor 7 is preferably maintained between about 100° C. and about 200° C. The lower limit of the temperature range is selected to prevent moisture condensation. The upper limit of the temperature range is selected based on the specific characteristics of sensor 7. Shottky diode 28 is integrated into a circuit comprising power source 30, voltmeter 31, and resistor 32.

Hydrogen dissolved in water is detectable with the presently preferred embodiment of hydrogen analyzer 38 down to concentrations of about 0.1 nM using the Shottky diode type sensor 7 described herein. This sensor is especially suited for detection of low hydrogen concentrations but can be used to measure dissolved hydrogen concentrations up to about 100 nM. Hydrogen analyzer 38 of the present invention can also be readily modified to detect higher concentrations of dissolved hydrogen.

To the best of the inventor's knowledge, output from the Shottky diode in the present invention is utilized in a novel manner. Typically solid state sensors for hydrogen yield a steady state output voltage that is directly related to the hydrogen concentration. However, in the presence of trace levels of hydrogen contained in a carrier gas devoid of oxygen, these sensors have been observed to be incapable of attaining a steady state voltage output within a reasonable timeframe. Rather the output increases continuously and the rate at which this output increases is linearly related to the hydrogen concentration. The reasons for this unexpected observation appear to be kinetic and diffusional limitations that occur at low hydrogen concentrations.

Thus, during Stage E, the output from sensor 7 is monitored over a period of time and the rate of voltage increase is calculated. This rate is compared to a calibration curve in order to quantify the hydrogen concentration. For example, a concentration of 0.1 ppm hydrogen yields a rate of approximately 10 millivolts per minute, a concentration of 1.0 ppm hydrogen yields a rate of approximately 100 millivolts per minute, and a concentration of 10 ppm hydrogen yields a rate of approximately 1,000 millivolts per minute. The carrier gas hydrogen concentrations can then be related to dissolved hydrogen concentrations in water by Henry's law coefficients (R. H. Perry and C. H. Chilton, *Chemical Engineers' Handbook*, McGraw-Hill Book Company, New York, P. 3–97. (1973)) or Ostwald coefficients (P. Gerhardt, R. G. E. Murray, W. A. Wood, and N. R. Krieg, *Methods for General and Molecular Bacteriology*, American Society for Microbiology. Washington D.C., pp. 145 and 184 (1994)). For example, at 20° C., Henry's coefficient for hydrogen in water is $6.83 \times 10^4$ atmospheres. The dissolved hydrogen concentration in water is calculated by the following equation:

$$C_L = 10^9 P_A C_G C_W / H$$

where $C_L$ is the dissolved hydrogen concentration in liquid water in units of nM, $10^9$ is for conversion from units of M to nM, $P_A$ is the ambient pressure in units of atmospheres (typically equal to 1), $C_G$ is the hydrogen concentration measured in the carrier gas in units of ppm, $C_W$ is the concentration of pure water in molarity (M) units and is equal to 55.6 M, and H is Henry's constant in units of atmospheres. H is temperature-dependent and at 20° C. this equation can be reduced for most applications to:

$$C_L = 0.81 C_G$$

At 10° C. the equation can be reduced to:

$$C_L = 0.87 C_G$$

Figure 4:
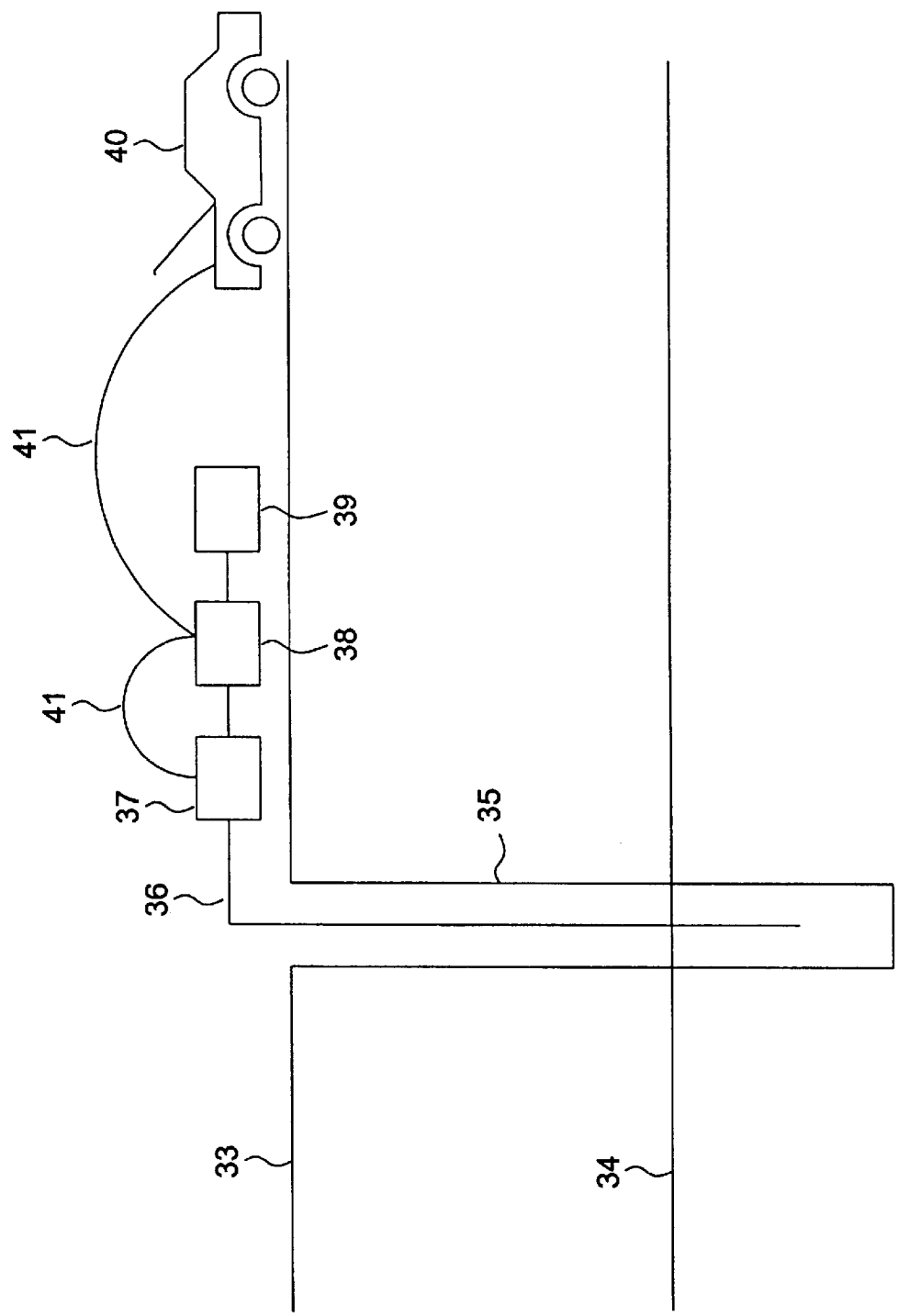
FIG. 4 shows a representative application of the hydrogen analyzer of the present invention to measure the concentration of dissolved hydrogen in groundwater.

Finally, FIG. 4 depicts field application of hydrogen analyzer 38 of the present invention for measurement of dissolved hydrogen in groundwater. Contaminated ground 33 includes groundwater at level 34 and a groundwater monitoring well 35. Groundwater is pumped through tubing 36 via pump 37 to dissolved hydrogen analyzer 38 which discharges to waste container 39. Pump 37 and dissolved hydrogen analyzer 38 are powered by a 12-volt battery in automobile 40 via jumper cables 41. Typically, the total time required to complete Stages A–E and obtain a measurement of the concentration of dissolved hydrogen is approximately 15–20 minutes.

Hydrogen analyzer 38 of the present invention has numerous uses. In general, the concentration of dissolved hydrogen can be used to monitor the nature, extent, rate, or stability of anaerobic biological systems.

Natural attenuation, also known as passive remediation or intrinsic remediation, is based on the natural ability of microorganisms present in groundwater to biodegrade environmental contaminants. Different microorganisms are capable of mediating these biodegradation processes. One method of classification of these bacteria is by the type of terminal electron accepting process (TEAP) used during oxidation of organic contaminants. For example, the aerobic TEAP is employed by bacteria using oxygen as the terminal electron acceptor. Different TEAPs are employed by anaerobic bacteria. Anaerobic TEAPs include denitrification, manganese reduction, ferric iron reduction, sulfidogenesis, and methanogenesis. Knowledge of which TEAPs exist in a given aquifer is important with respect to understanding biodegradation processes that are occurring.

Dissolved hydrogen concentration is an indicator of the type of TEAPs that are present in a body of water. Dissolved hydrogen concentrations ranging from 0.1–1.0 nM are associated with the iron-reducing TEAP, dissolved hydrogen concentrations ranging from 2–6 nM with the sulfidogenic TEAP, and dissolved hydrogen concentrations ranging from 10–20 nM with the methanogenic TEAP (F.H. Chapelle and P. B. McMahon, *J. Hydrology*, 127:85–108 (1991)). One application of the present invention is to measure dissolved hydrogen concentrations in groundwater at contaminated sites. Measurement of dissolved hydrogen allows determination of the types of TEAPs that are present, and thus provides information about specific biodegradation processes. For example, reductive dechlorination is one mechanism of biodegradation of chlorinated organic contaminants. These contaminants can include trichloroethene (TCE) among others. Reductive dechlorination of TCE via a biological mechanism can involve the pathway: TCE→cDCE→VC→$CO_2$ where cDCE is cis-dichloroethene, VC is vinyl chloride, and $CO_2$ is carbon dioxide. The first two reactions (TCE→cDCE→VC) are based on reductive dechlorination and typically occur in methanogenic and sulfidogenic TEAPs. The last reaction (VC→$CO_2$) is known to occur in the iron-reducing TEAP. Knowledge of which TEAPs exist in different zones of an aquifer can indicate which of these reactions are occurring at a site.

Enhancement of reductive dechlorination can also be accomplished by increasing or adjusting the dissolved hydrogen concentration in groundwater to a desired level. Dissolved hydrogen can be adjusted by sparging a mixture of hydrogen in nitrogen into groundwater thereby increasing the dissolved hydrogen concentration. Dissolved hydrogen can also be adjusted by adding the lactic acid-based preparation known as Hydrogen Release Compound (HRC) manufactured by Regenesis (San Juan Capistrano, Calif.). Lactic acid is slowly released by this preparation and is subsequently consumed by anaerobic bacteria that generate hydrogen. No matter how dissolved hydrogen in groundwater is adjusted, a means for measurement is required. The present invention can be used to measure dissolved hydrogen in such an application and thus facilitate accurate hydrogen concentration adjustment.

Anaerobic digesters are used to biodegrade waste water containing various organic compounds. These digesters employ consortia of anaerobic bacteria to accomplish the overall reaction: Organic matter →$CO_2$+$CH_4$ where $CO_2$ is carbon dioxide and $CH_4$ is methane. Instability of these consortia and thus of the digestor is a major problem in waste water treatment. Digestors commonly become unstable and "go sour" which is attributable to excess acid production. Measurement of pH is not a useful process variable for controlling digestor stability because it does not indicate instability at a sufficiently early point in time. Dissolved hydrogen concentration is a better indicator of digestor stability and is useful as a process variable to be used in a process control algorithm. Dissolved hydrogen has been described as an "ideal variable" for monitoring and control of anaerobic systems (J.-C. Frigon and S. R. Guiot, *Enzyme Microb. Technol.*, 17:1080–1086 (1995)). Nonetheless, the dissolved hydrogen may be present at concentrations less than 100 ppm (W. R. Slater, M. Merigh, N. L. Ricker, F. Labib, J. F. Ferguson, and M. M. Benjamin, *Wat. Res.*, 24:121–123 (1990)). The present invention, which is capable of sensing dissolved hydrogen down to a concentration of about 0.1 nM, is thus useful for monitoring digestor stability.

Many useful biochemical products are produced in bioreactors that employ microorganisms. Many of these bioreactors are operated anaerobically. Examples of biochemical products produced in bioreactors that employ microorganisms include antibiotics, amino acids, proteins, vitamins, growth regulators, hormones, steroids, beer, and wine. Control of these processes is often difficult because the process variables are not easily measured. For example, antibiotics are sometimes measured using a bioassay that requires an inordinate amount of time for completion. Such assays are not amenable to incorporation into process control strategies. Surrogate process variables are of interest in the biochemical process industry and include pH, carbon dioxide evolution rate, and carbon source concentration, among others. These surrogate process variables are incorporated into a process control algorithm to enable prediction of biochemical reaction extent or rate. Dissolved hydrogen is another process variable that is usefull in this regard and has been used to evaluate antibiotic susceptibility (E. G. Homnsten, H. Elwing, E. Khilstrom, and I. Lundstrom, *J. Antimicrobial Therapy*, 15:695–700 (1985)) and bioreactor mixing inhomogeneity (N. Cleland, E. G. Horsten, H. Elwinng, S.-O. Enfors, and I. Lundstrom, *Appl. Microbiol. Biotechnol.*, 20:268–270 (1984)). Pd-MOS sensors have been used for these applications but may not be applicable in cases where hydrogen sulfide, carbon monoxide, or oxygen are present In these cases, hydrogen analyzer 38 of the present invention will be useful.

Subsurface permeable walls composed of iron filings or other metallic materials are a usefull remediation tool for chlorinated solvent plumes in aquifers. These metal-reactive walls promote reductive dechlorination by anaerobic corrosion processes that produce hydrogen. The rates of corrosion and reductive dechlorination are related to the rate of hydrogen production (E. Reardon, *Environ. Sci. Technol.*, 29:2936–2945 (1995)). Dissolved hydrogen concentrations are a potentially important parameter that can be used to monitor the rate or extent of such processes. These metal-reactive walls are in effect consumed over time because of corrosion. In addition, the rate can decrease due to passivation of the metal surfaces. Thus measurement of dissolved hydrogen can also be used to monitor the status of these metal-reactive walls. Upon a significant decrease in dissolved hydrogen concentration, for example, the metal-reactive wall may be in need of regeneration or replacement. The present invention will be useful for making these determinations.

Dissolved hydrogen can be used as an indicator of corrosion. Hydrogen is formed from water when metals undergo corrosion in the absence of oxygen. Hydrogen can also cause embrittlement stress cracking corrosion (SCC) of stainless steels. Measurement of dissolved hydrogen to assess and monitor corrosion is another use for the present invention. Monitoring of corrosion pertains to operation of process equipment, pipelines, boilers, and any metal system that involves the processing, storage, or conveyance of water-based liquids.

While the presently preferred use of the present invention is measurement of dissolved hydrogen in aqueous solution, measurement of dissolved hydrogen in nonaqueous liquids such as transformer oil is possible.

The following examples merely illustrate the various embodiments now contemplated for practicing the invention, but should not be construed to limit the invention.

EXAMPLE 1

Dissolved Hydrogen Transfer to Gaseous Nitrogen Across NeoMecs GT-0204005 Hollow Fiber Membrane Module Groundwater containing different concentrations of dissolved hydrogen was circulated through a NeoMecs GT-0204005 hollow fiber gas membrane module. This module contains 0.5 square feet of membrane surface area. The water containing dissolved hydrogen was pumped through the shell of the module at a flow rate of 220 milliliters per minute. A volume of 12 milliliters of nitrogen gas was circulated through the lumen of the hollow fibers at a flow rate of 5,000–7,000 milliliters per minute.

The concentration of dissolved hydrogen in the water was determined using the bubble strip method in conjunction with a reduction gas analyzer (F. H. Chapelle and P. B. McMahon, *J. Hydrology*, 127:85–108 (1991)). This concentration is reported in Table I as $C_G$, the equilibrated gas-phase hydrogen concentration in ppm. Table I shows that an equilibrated gas-phase hydrogen concentration of 0.43 ppm (equivalent to 0.34 nM dissolved hydrogen) equilibrated across the hollow fiber membrane module in 4 minutes. An equilibrated gas-phase hydrogen concentration of 87 ppm (equivalent to 70 nM dissolved hydrogen) equilibrated across the hollow fiber membrane module in 6 minutes.

TABLE I

Gas-Phase Hydrogen Concentration (ppm) Transferred Across NeoMecs GT-0204005 Hollow Fiber Membrane Module

| Bubble Strip Hydrogen Concentration $C_G$ | Time (minutes) | | | |
|---|---|---|---|---|
| (ppm) | 0 | 2 | 4 | 6 |
| 0.43 | 0.15 | 0.36 | 0.41 | — |
| 87 | 1.5 | 47 | 72 | 90 |

EXAMPLE 2

Hydrogen Sensor Response (mV/min) in Presence of Oxygen or Carbon Monoxide in Nitrogen Carrier Gas A Shottky diode MIS hydrogen sensor containing an alumina insulator and a palladiun/silver metal gate was fabricated and tested for hydrogen sensitivity in nitrogen containing oxygen and carbon monoxide. The sensor temperature was controlled at 143° C. for these tests. Table II shows the response of the sensor to hydrogen in nitrogen as Test 1. The response was significantly lower in the presence of low concentrations of oxygen (Test 2) or carbon monoxide (Test 3).

TABLE II

Hydrogen Sensor Response (mV/min) in Presence of Oxygen and Carbon Monoxide in Nitrogen Carrier Gas

| | | Gas Phase Hydrogen Concentration (ppm) | | |
|---|---|---|---|---|
| Test | Conditions | 0.1 | 1 | 10 |
| 1 | Control | 49 | 252 | 2173 |
| 2 | 0.5% $O_2$ | 2.9 | 38.2 | 546.5 |
| 3 | 0.1% CO | −6.3 | 34.8 | 87.9 |

EXAMPLE 3

Removal of Oxygen and Carbon Monoxide from Carrier Gas

Oxygen and carbon monoxide removal from nitrogen carrier gas was tested with different compositions capable of removing oxygen and carbon dioxide, and gaseous hydrogen concentrations were monitored. The ascorbic acid-based preparation named Anaeropack manufactured by Mitsubishi Gas Chemical Corporation (MGC) America, Inc. (New York, N.Y.) was used for oxygen scavenging and the copper oxide-based preparation named Catalyst R3–11 manufactured by BASF Corporation was used for carbon monoxide scavenging. Anaeropack was used as purchased and was placed in a plastic module through which carrier gas flowed. Catalyst R3–11 was used as purchased and was placed in a brass pipe through which carrier gas flowed and heated to a constant temperature of 70° C. A 500-milliliter volume of nitrogen carrier gas containing oxygen was circulated and gas samples were collected and analyzed on a gas chromatograph for oxygen and on a reduction gas analyzer for hydrogen and carbon monoxide.

Table III shows results for a control test (Test 1) where no scavengers were used, a second test (Test 2) where only the oxygen scavenger was used, and a third test (Test 3) where both scavengers were used. The results show that oxygen was not removed in Test 1. Oxygen was removed to 0% in Test 2 and hydrogen did not increase significantly. The carbon monoxide concentration did increase significantly due to reaction of oxygen with the oxygen scavenging preparation. Test 3 shows that in the presence of both scavengers oxygen and carbon monoxide were both removed. During Test 3 hydrogen did not increase significantly.

TABLE III

Removal of Oxygen and Carbon Monoxide from Carrier Gas

| | | Concentration | | | | | |
|---|---|---|---|---|---|---|---|
| | | Oxygen (%) | | Hydrogen (ppm) | | Carbon Monoxide (ppm) | |
| Test | Conditions | Initial | Final | Initial | Final | Initial | Final |
| 1 | Control | 2.6 | 2.9 | 1.87 | 1.97 | 1.2 | 1.3 |
| 2 | $O_2$ Scavenger | 2 | 0 | 0.23 | 0.25 | 1.6 | 15 |
| 3 | $O_2$ & CO Scavengers | 2 | 0 | 0.18 | 0.21 | 0.65 | 0 |

EXAMPLE 4

Effect Of Water On Carbon Monoxide Removal by Catalyst R3–11

The effect of water on carbon monoxide removal by copper oxide-based Catalyst R3–11 was tested. A quantity of R3–11 was placed in a steam autoclave and treated for 15 minutes at 121° C. to saturate the catalyst with water vapor. The catalyst was then placed in a brass module through which gas flowed and was heated to 70° C. A 10-milliliter volume of nitrogen carrier gas was circulated through the heated catalyst and 0.1 milliliter of carbon monoxide was injected into the carrier gas. Carbon monoxide concentration was monitored over time. Table IV shows that carbon monoxide concentration did not decrease significantly over four minutes. A control test where new Catalyst R3–11 was used and was not treated in the autoclave demonstrated significant removal of carbon monoxide from the carrier gas in less than four minutes as shown in Table IV.

TABLE IV

Effect of Water on Carbon Monoxide Concentration (ppm) in Presence of Catalyst R3-11

| | Time (minutes) | | | |
|---|---|---|---|---|
| Condition | 0 | 2 | 2.5 | 4 |
| Control | 2,900 | 14 | — | 1.3 |
| Water | 1,200 | — | 610 | 530 |

In practice, water removal from carrier gas is preferred because of humidity that is created during equilibration of groundwater with the carrier gas in the hollow fiber membrane module, and because the ascorbic acid-based oxygen removal preparation is moist and releases moisture during use. Use of drying agents such as molecular sieves have proven to be useful in this regard. Tests using Catalyst R3–11 in combination with 13× molecular sieves to remove water from carrier gas show that carbon monoxide removal is sustained for at least 20 cycles of oxygen removal. Use of Catalyst R3–11 in the absence of 13× molecular sieves results in dramatic reduction of carbon monoxide removal capability within two to three cycles.

EXAMPLE 5

Analysis of Groundwater Containing Dissolved Hydrogen

Groundwater containing dissolved hydrogen was analyzed using dissolved hydrogen analyzer 38 depicted in FIG. 1 and results were compared to the bubble strip/reduction gas analyzer method. The groundwater was removed from a former manufacturing facility contaminated with chlorinated hydrocarbons. cis-1,2-Dichloroethene (cDCE) and vinyl chloride (VC) are the predominant contaminants present in groundwater. Groundwater samples were collected using a pneumatic bladder pump at a volumetric flow rate of 1,000 milliliters per minute. The actual dissolved hydrogen concentrations were as shown in Table V. Hydrogen analyzer 38 was operated with Stage A (sensor preparation) for 2 minutes, Stage B (nitrogen purge) for 1 minute, Stage C (hydrogen equilibration) for 3 minutes, Stage D (carrier gas preparation), and Stage E (measurement). Catalyst R3–11 was operated at 70° C. The sensor was operated at 117° C. for these tests. Table V shows analyzer 38 was capable of measuring dissolved hydrogen with a percent error ranging from −6.2% to 14%.

TABLE V

Hydrogen Analyzer Results with Groundwater Samples

| | Hydrogen Concentration (nM) | | |
|---|---|---|---|
| Test | Actual | Analyzer | Difference (%) |
| 1 | 1.4 | 1.6 | 14.3% |
| 2 | 0.96 | 1 | 4.2% |
| 3 | 0.96 | 0.9 | −6.2% |

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A hydrogen analyzer comprising in gaseous communication:

a mass transfer unit, having a liquid portion and a gaseous portion, through which hydrogen gas is transferred from a liquid analyte to a carrier gas;

a gas equilibrium reservoir within which hydrogen gas transferred from the analyte is equilibrated;

an oxygen unit for removal of oxygen from the carrier gas containing hydrogen;

a hydrogen sensor for measuring the amount of hydrogen in the carrier gas from which oxygen has been removed, wherein the hydrogen sensor is capable of detecting hydrogen in carrier gas equilibrated with hydrogen dissolved in an aqueous medium at a concentration of on the order of 0.1 nM; and a pump for moving the carrier gas through the mass transfer unit, gas equilibrium reservoir, oxygen unit and hydrogen sensor, all of which are connected in fluid flow communication.

2. The hydrogen analyzer of claim 1, further comprising a carbon monoxide unit for removal of carbon monoxide from the carrier gas containing hydrogen.

3. The hydrogen analyzer of claim 2, further comprising a sulfur unit for removing sulfur compounds from the carrier gas containing hydrogen.

4. The hydrogen analyzer of claim 1, further comprising a sulfur unit for removing sulfur compounds from the carrier gas containing hydrogen.

5. A hydrogen analyzer comprising in gaseous communication:

a mass transfer unit, having a liquid portion and a gaseous portion, through which hydrogen gas is transferred from a liquid analyte to a carrier gas;

a gas equilibrium reservoir within which hydrogen gas transferred from the analyte is equilibrated;

an oxygen unit for removal of oxygen from the carrier gas containing hydrogen;

a hydrogen sensor for measuring the amount of hydrogen in the carrier gas from which oxygen has been removed;

a pump for moving the carrier gas through the mass transfer unit, gas equilibrium reservoir, oxygen unit and hydrogen sensor, all of which are connected in fluid flow communication;

a carbon monoxide unit for removal of carbon monoxide from the carrier gas containing hydrogen; and a sulfur unit for removing sulfur compounds from the carrier gas containing hydrogen, wherein the sulfur and carbon monoxide removal units comprise a unit including a composition that is capable of removing both carbon monoxide and sulfur compounds from the carrier gas.

6. The hydrogen analyzer of claim 5, wherein the gas equilibrium reservoir is defined by the sulfur and carbon monoxide removal unit.

7. The hydrogen analyzer of claim 5, wherein the carbon monoxide and sulfur compound removal composition is catalyst R3–11.

8. The hydrogen analyzer of claim 7, further comprising a heater coupled to heat the carrier gas containing hydrogen to a temperature of 55° C. to 80° C. as the carrier gas flows through the carbon monoxide unit.

9. The hydrogen analyzer of claim 6, further comprising a moisture removal unit for removing moisture from the carrier gas.

10. The hydrogen analyzer of claim 9, wherein the moisture removal unit further comprises a moisture-removal composition selected from the group consisting of molecular sieves and a calcium sulfate preparation.

11. The hydrogen analyzer of claim 6, wherein the carbon monoxide and sulfur compound removal composition is a catalyst preparation comprising magnesium dioxide, copper oxide and aluminum oxide.

12. A hydrogen analyzer comprising in gaseous communication:

a mass transfer unit, having a liquid portion and a gaseous portion, through which hydrogen gas is transferred from a liquid analyte to a carrier gas;

a gas equilibrium reservoir within which hydrogen gas transferred from the analyte is equilibrated;

an oxygen unit for removal of oxygen from the carrier gas containing hydrogen;

a hydrogen sensor for measuring the amount of hydrogen in the carrier gas from which oxygen has been removed;

a pump for moving the carrier gas through the mass transfer unit, gas equilibrium reservoir, oxygen unit and hydrogen sensor, all of which are connected in fluid flow communication;

a carbon monoxide unit for removal of carbon monoxide from the carrier gas containing hydrogen; and a heater coupled to heat the carrier gas containing hydrogen as the carrier gas flows through the carbon monoxide unit.

13. A hydrogen analyzer comprising in gaseous communication:

a mass transfer unit, having a liquid portion and a gaseous portion, through which hydrogen gas is transferred from a liquid analyte to a carrier gas, wherein the mass transfer unit is selected from the group consisting of a hollow fiber gas transfer module and a sparger;

a gas equilibrium reservoir within which hydrogen gas transferred from the analyte is equilibrated;

an oxygen unit for removal of oxygen from the carrier gas containing hydrogen;

a hydrogen sensor for measuring the amount of hydrogen in the carrier gas from which oxygen has been removed;

a pump for moving the carrier gas through the mass transfer unit, gas equilibrium reservoir, oxygen unit and hydrogen sensor, all of which are connected in fluid flow communication.

14. A hydrogen analyzer comprising in gaseous communication:

a mass transfer unit, having a liquid portion and a gaseous portion, through which hydrogen gas is transferred from a liquid analyte to a carrier gas;

a gas equilibrium reservoir within which hydrogen gas transferred from the analyte is equilibrated;

an oxygen unit for removal of oxygen from the carrier gas containing hydrogen, wherein the oxygen removal unit comprises an oxygen removal composition;

a hydrogen sensor for measuring the amount of hydrogen in the carrier gas from which oxygen has been removed; and a pump for moving the carrier gas through the mass transfer unit, gas equilibrium reservoir, oxygen unit and hydrogen sensor, all of which are connected in fluid flow communication.

15. The oxygen removal component of claim 14, wherein the oxygen removal unit is an ascorbic acid derivative.

16. The hydrogen analyzer of claim 14, wherein the hydrogen sensor comprises a metal oxide semiconductor.

17. A hydrogen analyzer comprising in gaseous communication:
- a mass transfer unit, having a liquid portion and a gaseous portion, through which hydrogen gas is transferred from a liquid analyte to a carrier gas;
- a gas equilibrium reservoir within which hydrogen gas transferred from the analyte is equilibrated;
- an oxygen unit for removal of oxygen from the carrier gas containing hydrogen;
- a hydrogen sensor for measuring the amount of hydrogen in the carrier gas from which oxygen has been removed, wherein the hydrogen sensor is selected from the group consisting of a Shottky diode and a field effect transistor; and
- a pump for moving the carrier gas through the mass transfer unit, gas equilibrium reservoir, oxygen unit and hydrogen sensor, all of which are connected in fluid flow communication.

18. A hydrogen analyzer comprising in gaseous communication:
- a mass transfer unit, having a liquid portion and a gaseous portion, through which hydrogen gas is transferred from a liquid analyte to a carrier gas;
- a gas equilibrium reservoir within which hydrogen gas transferred from the analyte is equilibrated;
- a carbon monoxide unit for removal of carbon monoxide from the carrier gas containing hydrogen;
- an oxygen unit for removal of oxygen from the carrier gas containing hydrogen;
- a sulfur unit for removing sulfur compounds from the carrier gas containing hydrogen;
- a moisture unit for removing moisture from the carrier gas;
- a hydrogen sensor for measuring the amount of hydrogen in the carrier gas from which carbon monoxide, oxygen, sulfur compounds and moisture have been removed, said hydrogen sensor being capable of detecting hydrogen in carrier gas equilibrated with hydrogen dissolved in an aqueous medium at a concentration of on the order of 0.1 nM; and
- a pump for moving the carrier gas through the mass transfer unit, gas equilibrium reservoir, carbon monoxide, oxygen, sulfur and moisture units and hydrogen sensor, all of which are connected in fluid flow communication.

19. A hydrogen analyzer comprising in gaseous communication:
- a mass transfer unit, having a liquid portion and a gaseous portion, through which hydrogen gas is transferred from a liquid analyte to a carrier gas;
- a gas equilibrium reservoir within which hydrogen gas transferred from the analyte is equilibrated;
- an oxygen unit for removal of oxygen from the carrier gas containing hydrogen that neither produces nor consumes hydrogen;
- a hydrogen sensor for measuring the amount of hydrogen in the carrier gas from which oxygen has been removed; and
- a pump for moving the carrier gas through the mass transfer unit, gas equilibrium reservoir, oxygen unit and hydrogen sensor, all of which are connected in fluid flow communication.

* * * * *

UNITED STATES PATENT AND TRADEMARK OFFICE
CERTIFICATE OF CORRECTION

PATENT NO. : 6,277,329 B1  Page 1 of 1
DATED : August 21, 2001
INVENTOR(S) : P.J. Evans It is certified that error appears in the above-identified patent and that said Letters Patent is hereby corrected as shown below:

<u>Title page,</u>
*Assistant Examiner*, "B. R Gordon" should read -- Brian R. Gordon --

Item [56], References Cited, OTHER PUBLICATIONS, insert in appropriate order the following:
-- Carus Chemical Company, Product Data Sheet for Carulite 300 Catalyst, 13 pp. --

<u>Column 19,</u>
Line 63, "claim 6," should read -- claim 5, --

<u>Column 20,</u>
Line 3, "claim 6," should read -- claim 5, --
Line 43, "removed;" should read -- removed; and --

Signed and Sealed this

Thirteenth Day of August, 2002

*Attest:*

JAMES E. ROGAN
*Director of the United States Patent and Trademark Office*

*Attesting Officer*